United States Patent [19]
Whitekettle et al.

[11] Patent Number: 4,970,239
[45] Date of Patent: Nov. 13, 1990

[54] METHOD FOR CONTROLLING MACROINVERTEBRATES UTILIZING DECYLTHIOETHYLAMINE

[75] Inventors: Wilson K. Whitekettle, Conroe, Tex.; Larry A. Lyons, Woodbury, N.J.

[73] Assignee: Betz Laboratories, Inc., Trevose, Pa.

[21] Appl. No.: 433,803

[22] Filed: Nov. 9, 1989

[51] Int. Cl.$^5$ ............................................. A01N 33/08
[52] U.S. Cl. .................................................. 514/665
[58] Field of Search ............................. 514/665; 71/67

[56] References Cited

U.S. PATENT DOCUMENTS

| | | | |
|---|---|---|---|
| 2,818,365 | 12/1957 | Deebel et al. | 514/665 |
| 4,328,638 | 5/1982 | Smithson | 43/124 |
| 4,462,914 | 7/1984 | Smith | 210/755 |
| 4,561,983 | 12/1985 | Davis et al. | 210/755 |
| 4,579,665 | 4/1986 | Davis et al. | 210/755 |
| 4,816,061 | 3/1989 | Walter, Jr. et al. | 71/67 |
| 4,816,163 | 3/1989 | Lyons et al. | 210/698 |
| 4,857,209 | 8/1989 | Lyons et al. | 210/755 |

OTHER PUBLICATIONS

"Bivalve Fouling of Nuclear Power Plant Service", U.S. Nuclear Regulatory Commission 1984.
"Freshwater Macrofouling and Control with Emphasis on Corbicula", Dec. 1983 Proceedings of Electric Power Research Institute.
"Clams—A Growing Threat to Inplant Water Systems", Plant Engineering, Jun. 1979, p. 165.

*Primary Examiner*—Douglas W. Robinson
*Assistant Examiner*—Kevin E. Weddington
*Attorney, Agent, or Firm*—Alexander D. Ricci; Roslyn T. Tobe

[57] ABSTRACT

A method of controlling the fouling potential of macroinvertebrates, such as mollusks in aqueous systems which comprises adding to the system an effective controlling amount of an alkylthioalkylamine or acid addition salt thereof.

10 Claims, No Drawings

METHOD FOR CONTROLLING MACROINVERTEBRATES UTILIZING DECYLTHIOETHYLAMINE

BACKGROUND OF THE INVENTION

This invention relates to the control of fouling by macroinvertebrates, especially mollusks, in aqueous systems by utilizing an n-alkylthioalkylamine having a carbon chain length of 5–18 carbon atoms or acid addition salt thereof.

More particularly, this invention relates to control of potential macroinvertebrate fouling in cooling systems for both industrial plants and utilities which are subject to such fouling, whether the system is using cooling water on a once-through basis or on a recirculating basis. The once-through systems operate by drawing cooling water through the process to be cooled on a one-time basis and discharging the water directly to the receiving body with a short residence time (usually minutes to hours). In contrast, recirculating cooling systems require the addition of only a fraction of the system volume as makeup water. Additionally, the service water systems (waste, safety and auxiliary cooling) which are often a part of these cooling systems are also quite vulnerable to macroinvertebrate fouling, primarily because they do not run continuously, the conduits are of a smaller diameter, and more time is allowed for macroinvertebrate growth.

The extent and type of macroinvertebrate fouling will depend upon many factors such as the source of the cooling water, the season, the water temperature, the growth rate of the fouling macroinvertebrate, and the linear velocity of the cooling water. Because of the large quantities of cooling water used, the locality of the plant will dictate the water's source. A fresh water cooling system will be drawing water from a river, lake, or well, whereas plants situated along coastal areas will most likely utilize brackish or marine water for their systems.

Both once-through and recirculating types of cooling water are treated prior to entering the system by screening to remove objects which are large enough that they could damage pumps and heat exchange equipment. This screening does not prevent the passage of the early life-stages or larval stages of the macroinvertebrates which are the precursors to fouling as growth conditions are usually favorable within these systems. These early life stages of the macroinvertebrates will settle out in low flow areas or attach to substrate within the cooling system and grow to mature organisms.

For example, mollusks are common macroinvertebrates which can cause macrofouling problems to marine and fresh water cooling systems. Macrofouling by mollusks, like other groups of macrofouling macroinvertebrates—barnacles, bryozoans, sponges, hydroids, tunicates and annelids—is initiated by the settlement or attachment of larval and/or juvenile stages that are easily entrained by the service waters of cooling systems. Fouling caused by the settlement, attachment and/or biogrowth of the macroinvertebrates in the cooling systems and associated service water systems of the industrial plants and utilities which utilize large quantities of water is a major problem causing a variety of deleterious effects to the structure, operation and safety of these systems.

As indicated in the U.S. Nuclear Regulatory Commission 1984 Report entitled "Bivalve Fouling of Nuclear Power Plant Service—Water Systems", the safe operation of a nuclear power plant is a concern because of fouling caused by the Asiatic clam (more specifically *Corbicula fluminea*), the blue mussel (*Mytilus edulis*) and the American oyster (*Crassostrea virginica*). This report describes the correlations between the biology of these bivalve mollusks and the design and operation of power plants that allow bivalves to enter and reside within their cooling water systems.

One of the species of mollusks controlled by the method of this invention is the Asiatic clam, *Corbicula spp*. As indicated in the article entitled "Freshwater Macrofouling and Control with Emphasis on Corbicula" in the December 1983 Proceedings of the Electric Power Research Institute (EPRI), the Asiatic clam has caused significant incidents of macrofouling to fresh water cooling systems of power plants. Another freshwater mollusk, the Zebra mussel, more specifically *Dreissena polymorph*, causes fouling problems to cooling systems in a similar manner as the Asiatic clam. Both Dreissena and Corbicula have free floating planktonic veliger larvae which allow easy penetration into cooling systems. Similar macrofouling problems plague cooling systems using estuarine, brakish, or marine waters, but with different species of macroinvertebrates.

As a specific example of how a macroinvertebrate can cause fouling problems, a description of some characteristics of the Asiatic clam follows:

One-year-old clams are capable of plugging valves and nozzles. Two-year-old clams can cause mechanical damage to impellers and other moving parts of water-distribution systems. At six years, the clam can damage tires of construction vehicles. As in all other clams, growth is rapid in early years and then tapers off. "Clams - A Growing Threat to Inplant Water Systems", Plant Engineering, June 1979, p. 165.

The Asiatic clams are very tolerant of many chemicals and often occur in great abundance. They have accumulated to depths of two meters in the Delta-Mendota Canal in California and have caused reduction in water flow. Some industrial plants have difficulty obtaining fire insurance after inspectors found the fire protection systems plugged with Asiatic clam shells. Pump impellers have been damaged by shells in some industrial plants. The number of power plants which have experienced problems with this species has been steadily increasing during the past several years. Problems in fossil-fueled power plants most often relate to pluggage of condenser tubes, surface water heat exchangers, and blockage of fire protection systems. In addition to these problems, nuclear power plants may have other problems associated with the shutdown service water, and emergency reactor cooling systems.

Fouling control of macroinvertebrates, such as mollusks, has been attempted using physical/mechanical and chemical techniques (see, e.g., U.S. Pat. No. 4,328,638), but no foolproof combination has been developed.

Chlorine, a commonly used biofouling inhibiting agent, has several limitations with respect to treatment to control macroinvertebrates. Chlorine is very toxic to microorganisms and readily kills them at 1 or 2 mg/liter levels; however, Asiatic clams can survive for a considerable period of time in water containing a much higher level of chlorine because of their anatomic and physiological development relative to microorganisms. Microorganisms must accept the environment they find themselves in and live or die depending upon the nature of the environment. On the other hand, higher animals such as mollusks, and other macroinvertebrates when they find themselves in an environment that is inhospitable, can either move or utilize defense systems to exclude the hostile environment. For example, Asiatic clams can close their shells to exclude the hostile environment. Clams have very sensitive chemosensors in the mantle lining the edge of their shells and, even when their shells are tightly closed, they can continuously sample the environment to determine when it is safe to open up their shells and start siphoning again. A clam immersed in chlorine containing water so that its shell is bleached white will open up after the chlorine level drops and resume its life. As a result, biocides that are sensed by the clam's chemoreceptor organs as life threatening are not effective simply because the clam will close its shell until the threat passes. Clams can remain closed for days and still live and resume normal activity. For these reasons prolonged exposure to chlorine is required to achieve efficacy. Other limitations of chlorine treatment include the chlorine demand of the cooling water which reduces the potency of chlorine, and the strict environmental regulations being imposed which act to severely limit the discharge of chlorine residues, and in some cases seek to eliminate the use of chlorine entirely.

In addition to chlorine, Smith, U.S. Pat. No. 4,462,914 discloses the use of a high density cationic polymer to control Corbicula. While the polymer appears to be efficacious toward the adult clam after a six day exposure period, it suffers from some of the same drawbacks as chlorine.

The above-mentioned concerns over the potential environmental impact of biocides is well described by the following excerpt from the December 1983 Proceedings of the Electric Power Research Institute:

"Chemical controls have an inherent liability. What can kill inside the power plant may also impact the receiving water body; chemical toxicants are not specific. The perfect chemical would be stable enough to be effective inside the plant, but become non-toxic, via chemical reaction or decay, before or as it entered the receiving water body. So far, no chemical meets these specifications: chlorine and bisulfate/sulfide, which have actually been used in an attempt to control Corbicula fouling, have not been effective alone, or have been successful only under limited conditions. Such a chemical may not exist, but scheduling of application of a chemical at the beginning of scheduled outages may offer a less stringent alternative, because of the possibility of extending holdup times."

U.S. Pat. No. 4,561,983 discloses the use of nitrostyrene compound to control the fouling potential of mollusks. U.S. Pat. No. 4,579,665 discloses the use of a nitrostyrene compound and an alkyl thiocyanate compound to control mollusk fouling potential.

U.S. Pat. No. 4,816,163 discloses a method for controlling the fouling potential of macroinvertebrates, especially mollusks such as the Asiatic clam, in a aqueous system which comprises adding to the system an effective controlling amount of a water-soluble alkyl guanidine salt. U.S. Pat. No. 4,857,209 discloses a method for controlling the fouling potential of macroinvertebrates, especially mollusks such as the Asiatic clam, in a aqueous system which comprises adding to the system an effective controlling amount of a water-soluble quaternary ammonium salt with detergent properties. The most preferred compound is a water-soluble alkyl dimethyl benzyl ammonium chloride having an alkyl distribution of about 40% $C_{12}$, 50% $C_{14}$, and 10% $C_{16}$.

The compound of the present invention has been utilized for control of microorganisms, i.e., bacteria, fungi, and algae, in U.S. Pat. 4,816,061 but has not been suggested for control of larger more complex organisms, especially macroinvertebrates in aqueous systems.

Even though a compound may show biocidal efficiency against one class of organisms this does guarantee its efficacy against a different class of organisms. Critical differences exist between microorganisms, such as bacteria, fungi, and algae, and macroinvertebrates, such as the Asiatic clam in the level of anatomic and physiological complexity. Penicillin, for example, is toxic to bacteria but is not toxic to higher animals such as Asiatic clams or humans. Warfarin (Coumarin), on the other hand, is toxic to mammals, but not to bacteria.

Bacteria, fungi, and algae microorganisms are dependent upon the presence of metabolizable components in an aqueous system. However, the presence or absence of macroinvertebrates, such as mollusks, is essentially independent of the presence of metabolizable components in the water because they are much more complex organisms than microorganisms, both in terms of anatomic and physiological complexity and position in the food chain. Macroinvertebrates, such as mollusks, are unable to exist on metabolizable components. Rather macroinvertebrates require small plants or animals as foodstuff. Until the unexpected discovery of the applicants, the use of the compound of the present invention has never before been appreciated to control macroinvertebrates.

SUMMARY OF THE INVENTION

This invention is a method for controlling the fouling potential of macroinvertebrates, especially mollusks, such as the Asiatic clam and the Zebra mussel in an aqueous system prone to such fouling. The method comprises adding to the system a sufficient quantity of an n-alkylthioalkylamine or acid addition salt thereof to control such macrofouling.

DETAILED DESCRIPTION OF THE INVENTION

The present inventors discovered that the survival of macroinvertebrates, particularly mollusks, in an aqueous system could be significantly impaired by adding to the system a sufficient amount for the purpose of an n-alkylthioalkylamine having a carbon chain length of about 5-18 carbon atoms. The alkylthioalkylamine compound useful in the present invention has the formula:

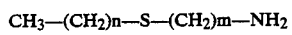

$$CH_3-(CH_2)_n-S-(CH_2)_m-NH_2$$

wherein n is an integer of from 4-17, preferably 6-12 and most preferably 9, and m is an integer of 2 or 3, preferably 2. The most preferred compound is a decylthioethylamine (DTEA). The acid addition salts of the alkylthioalkylamine can also be used in the present invention. DTEA is available from Dow Chemical Company under the name DTEA or XU 40304.01L.

The mollusks which are particularly affected by DTEA are the Asiatic clams, more specifically *Corbicula spp.* Other specific mollusks believed to be affected by DTEA are Zebra mussels. It is believed that not only mollusks, but also macrofouling macroinvertebrates can be controlled in accordance with this invention.

The term "macroinvertebrates" as used herein, is defined as the classes of aquatic organisms that develop from a juvenile or larval life stage form to adult life stage forms. Macroinvertebrates are complex multi-cellular organisms containing an integration of organs and tissues that make up advanced life support systems (i.e., circulatory, digestive, reproductive, nervous..). It is the result of the development of the adult life stages of macroinvertebrates that can cause many unique fouling problems to cooling systems. These problems are categorized under the term "macrofouling" meaning damaging equipment, jeopardizing safety related systems, reducing line pressure which can reduce cooling efficiency. Reducing cooling efficacy can jeopardize the system's equipment and reduce overall efficiency and revenue. Exemplary macroinvertebrates include mollusks (i.e., clams, mussels, oysters, and snailsl, crustaceans (i.e., barnacles), sponges, annelids, bryozoans, and tunicates. All of these macroinvertebrates share the characteristics listed above and have equivalent levels of organ system complexity.

In accordance with the present invention, the DTEA treatment may be added to the desired aqueous system in need of macrofouling control, in an amount from about 0.1 to about 1000 mg/L of the aqueous system to be treated. Preferably about 0.1 to about 100 mg/L of DTEA is added to the aqueous system in need of macrofouling control.

It is thought that DTEA may be combined with beta-bromo-beta-nitrostyrene; tri-n-butyl tetradecyl phosphonium chloride; n-alkyl (40% $C_{12}$, 50% $C_{14}$, 10% $C_{16}$) dimethyl benzyl ammonium chloride, 2-bromo, 2-nitropropane-1, 3-diol; 2, 2-dibromo-3-nitrilopropionamide; dodecylguanidine hydrochloride; methylene bis (thiocyanate); or 5-chloro-2-methyl-4-isothiazolin-one to exhibit satisfactory macrofouling control.

This invention may be used to control macroinvertebrate fouling in cooling systems for both industrial plants and utilities which are subject to such fouling, whether the system is using cooling water on a once-through basis or is of the recirculating type. This invention may also be used to control all life stages of the macroinvertebrates. For example, addition of DTEA in an effective amount to the incoming water of a once-through cooling system to destroy planktonic juveniles before such settle and form the adult clams or mollusks, provides adequate inhibition of clam infestation and the consequent build-up in the structural parts of the cooling water system. Furthermore, the destruction of adult clams could also be accomplished thereby eradicating fouling problems of a more mature nature.

While other biocidal materials do have some efficacy for instance, chlorine, chlorophenates, cationic polymers, and the like, these chemicals require long exposure periods to the macrofouling organism to achieve control. The present inventors, in reviewing macrofouling problems, were attempting to discover chemicals which would not only be effective in controlling macroinvertebrates, especially mollusks, but which would be effective with shorter exposure periods. Subsequently, reduced exposure periods of the chemicals to the cooling systems will provide not only a more economical means of treating the cooling systems, but also reduce the potential environmental concerns. Furthermore, the inventors were in search of chemicals that could be altered or neutralized during the application process to products that would cause less environmental concern by the natural constituents present in the cooling systems. There are many agents (for instance bacteria and other microorganisms, silt, clays, humic and organic acids, plus other anionic materials and polymers) which would provide assistance in neutralizing and eliminating toxic effects of the compounds prior to being discharged. The present inventors found that DTEA, in fact, provides all of these properties.

The following examples are provided to illustrate an embodiment of the invention and are not intended to restrict the scope thereof.

Static bioassays were conducted with the DTEA formulation on Corbicula ranging in size from 0.9 cm to 1.7 cm with examination of concentrations of 2.5, 5, 10, 25, and 50 mg/L. Glass beakers were used for each test solution. Six clams ranging in size from 0.9 cm to 1.7 cm, measured across the widest part of the shell, were placed into each of the beakers containing diluent water or toxicant. After an exposure period of 24 or 48 hours, a recovery period was initiated by transferring the remaining live clams to test vessels with only diluent water. Mortality responses were observed at the hourly intervals shown in the tables below. Mortality is defined as the point in time when the bivalve shell of the adult clam gapes open from the relaxed muscle tissue of the expired clam. All clams that were not actively siphoning at the end of the recovery period were opened up for microscopic examination to determine their viability or mortality. All clams were confirmed viable by the actively beating cilia lining the gill epithelium. Cumulative percent mortalities are provided in the tables below.

TABLE I (1) TEST SERIES 1: EXPOSURE PERIOD OF 48 HOURS
Size of Corbicula 0.9-1.6 cm

| Active Concentration mg/l | Cumulative % Mortality | | | | |
|---|---|---|---|---|---|
| | 24 hr | 31 hr | 48 hr | 72 hr | 144 hr |
| 50 | 0 | 0 | 42 | 100 | — |
| 25 | 8 | 8 | 75 | 100 | — |
| 10 | 25 | 50 | 100 | — | — |
| 5 | 0 | 17 | 50 | 83 | 83 |
| 2.5 | 0 | 0 | 0 | 0 | 0 |
| 0 (Control) | 0 | 0 | 0 | 0 | 0 |

TABLE II (2) TEST SERIES 2: EXPOSURE PERIOD OF 48 HOURS
Size of Corbicula: 1.0-1.7 cm

| Active Concentration mg/l | Cumulative % Mortality | | | | | |
|---|---|---|---|---|---|---|
| | 24 hr | 48 hr | 120 hr | 144 hr | 192 hr | 240 hr |
| 10 | 0 | 42 | 100 | — | — | — |
| 5 | 0 | 58 | 92 | 100 | — | — |
| 1 | 0 | 0 | 0 | 0 | 0 | 0 |
| 0 (Control) | 0 | 0 | 0 | 0 | 0 | 0 |

TABLE III (3) TEST SERIES 3: EXPOSURE PERIOD OF 24 HOURS
Size of Corbicula: 1.0-1.7 cm

| Active Concentration mg/l | Cumulative % Mortality | | | | | |
|---|---|---|---|---|---|---|
| | 24 hr | 48 hr | 120 hr | 144 hr | 192 hr | 240 hr |
| 10 | 0 | 25 | 75 | 75 | 75 | 75 |
| 5 | 0 | 67 | 75 | 75 | 75 | 75 |
| 1 | 0 | 0 | 0 | 0 | 0 | 0 |

TABLE III-continued

| (3) TEST SERIES 3: EXPOSURE PERIOD OF 24 HOURS Size of Corbicula: 1.0-1.7 cm | | | | | | |
|---|---|---|---|---|---|---|
| Active Concentration mg/l | Cumulative % Mortality | | | | | |
| | 24 hr | 48 hr | 120 hr | 144 hr | 192 hr | 240 hr |
| 0 (Control) | 0 | 0 | 0 | 0 | 0 | 0 |

While this invention has been described with respect to particular embodiments thereof, it is apparent that numerous other forms and modifications of this invention will be obvious to those skilled in the art.

The appended claims and this invention generally should be constructed to cover all such obvious forms and modifications which are within the true spirit and scope of the present invention.

What is claimed is:

1. A method for controlling the fouling potential of mollusks in an aqueous system of the type prone to such fouling, said method comprising adding to said aqueous system an effective amount from about 0.1 to about 1000 mg/l of said aqueous system an n-alkylthioalkylamine or acid addition salt thereof having the formula:

$$CH_3-(CH_2)_n-S-(CH_2)_m-NH_2$$

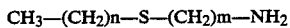

wherein n is an integer of from 4–17, and m is an integer of 2 or 3.

2. A method as recited in claim 1 wherein said mollusks are selected from the group consisting of clams, mussels and oysters.

3. A method as recited in claim 1 wherein said n-alkylthioalkylamine has the following structure $$CH_3-(CH_2)_n-S-(CH_2)_m-NH_2$$

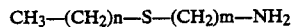

wherein n is an integer from 6–12 and m is 2 or 3.

4. A method as recited in claim 2 wherein said mollusks are selected from the group consisting of Asiatic clams and Zebra mussels.

5. A method as recited in claim 2 wherein said aqueous system is the aqueous system of a cooling water system.

6. A method as recited in claim 4 wherein said mollusks are Asiatic clams.

7. A method as recited in claim 4 wherein said mollusks are Zebra mussels.

8. A method as recited in claim 3 wherein said n-alkylthioalkylamine is decylthioethylamine.

9. A method as recited in claim 8 wherein said mollusks are comprised primarily of Corbicula.

10. A method as recited in claim 9 wherein said aqueous system is the aqueous system of a cooling water system.

* * * * *